(12) United States Patent
Douglas et al.

(10) Patent No.: US 9,151,753 B2
(45) Date of Patent: Oct. 6, 2015

(54) METHOD AND TEST STRIP FOR DETECTION OF RESIDUES

(75) Inventors: David W. Douglas, Kensington, NH (US); Robert J. Markovsky, Brentwood, NH (US)

(73) Assignee: Charm Sciences, Inc., Lawrence, MA (US)

( * ) Notice: Subject to any disclaimer, the term of this patent is extended or adjusted under 35 U.S.C. 154(b) by 908 days.

(21) Appl. No.: 13/379,558

(22) PCT Filed: Jun. 18, 2010

(86) PCT No.: PCT/US2010/039113
§ 371 (c)(1),
(2), (4) Date: Dec. 20, 2011

(87) PCT Pub. No.: WO2010/151485
PCT Pub. Date: Dec. 29, 2010

(65) Prior Publication Data
US 2012/0100638 A1 Apr. 26, 2012

Related U.S. Application Data

(60) Provisional application No. 61/219,190, filed on Jun. 22, 2009.

(51) Int. Cl.
*G01N 33/558* (2006.01)
*G01N 33/552* (2006.01)
*G01N 33/543* (2006.01)
*G01N 33/94* (2006.01)

(52) U.S. Cl.
CPC ........ *G01N 33/552* (2013.01); *G01N 33/54306* (2013.01); *G01N 33/9446* (2013.01)

(58) Field of Classification Search
None
See application file for complete search history.

(56) References Cited

U.S. PATENT DOCUMENTS

| | | | |
|---|---|---|---|
| 7,410,808 B1 * | 8/2008 | Saul et al. ..................... | 436/514 |
| 2008/0274566 A1 * | 11/2008 | Saul et al. ..................... | 436/518 |
| 2010/0081146 A1 | 4/2010 | Wei ............................... | 435/7.1 |

FOREIGN PATENT DOCUMENTS

WO     WO 2005057216 A1 *  6/2005

* cited by examiner

*Primary Examiner* — Chris L Chin
(74) *Attorney, Agent, or Firm* — MacCord Mason PLLC; Richard Long

(57) ABSTRACT

A method, test strip and method of manufacturing a test strip useful for detecting one or more analytes, such as an antibiotic, in a test sample such as a milk sample. The test strip and method include a labeled specific binder and test capture agent for the specific binder that increases test sensitivity to the analyte for which the specific binder has affinity while decreasing test sensitivity to an analyte for which a multianalyte binder has affinity.

32 Claims, 6 Drawing Sheets

METHOD AND TEST STRIP FOR DETECTION OF RESIDUES

REFERENCE TO PRIOR APPLICATIONS

This application claims priority to and incorporates by reference U.S. Provisional Application No. 61/219,190, filed Jun. 22, 2009.

BACKGROUND OF THE INVENTION

Antibiotic residues in foods are a major food safety concern. Health issues include bacterial resistance to drugs and allergic reactions. Food is tested worldwide for antibiotics and other contaminants. Immunochromatographic test devices, such as lateral flow test strips, are often used to perform such testing and are well known in the art. Examples of such devices and related methods are described in U.S. Pat. Nos. U.S. Pat. No. 7,410,808, issued Aug. 12, 2008 and U.S. Pat. No. 5,985,675, issued Nov. 16, 1999; U.S. Pat. No. 6,319,466, issued Nov. 20, 2001, and U.S. patent application Ser. No. 10/289,089, filed Nov. 6, 2002 (based on U.S. Provisional Application 60/332,877, filed Nov. 6, 2001); and U.S. patent application, the teachings of which are incorporated herein by this reference.

Lateral-flow test strips can be configured to detect one or more analytes in a fluid sample such as a milk sample. Such strips typically include a capture agent immobilized within a defined region of the test strip, variously referred to as a test line or a test zone and/or a control zone or control line. The capture agent of choice has binding affinity for a reagent that is in a mobile phase of the test strip. If the mobile-phase reagent is detectably labeled, a detectable signal can be generated within the region of the test strip in which the mobile-phase reagent binds to the capture agent.

The sensitivity and specificity of a test device or method relative to a particular analyte relates to the binding affinity between the analyte and a binder. If the binder and analyte have good affinity, analyte-binder complex will form readily. In the case of a multianalyte binder—a binder that has affinity to more than one analyte—the affinity of certain analytes to the binder may be different than others. In addition, the particular affinity of a particular analyte to a chosen binder may not reflect the desired detection level for that analyte. In those cases, it is desired to adjust the test sensitivity to the particular analyte. For example, U.S. Pat. No. 6,319,466 describes a test device and method for detecting an analyte at reduced sensitivity levels.

We describe herein a method and device for decreasing test sensitivity to one or more analytes for which a multianalyte binder is overly affinitive relative to the desired detection level for one or multiple analytes. If there is too much affinity, the test will be overly sensitive. By reducing the test sensitivity to such analytes, while either maintaining or increasing test sensitivity to another analyte to which the multianalyte binder has affinity, the test can be adapted to detect analytes at desired levels, such as desired regulatory levels.

SUMMARY

Figure 1:
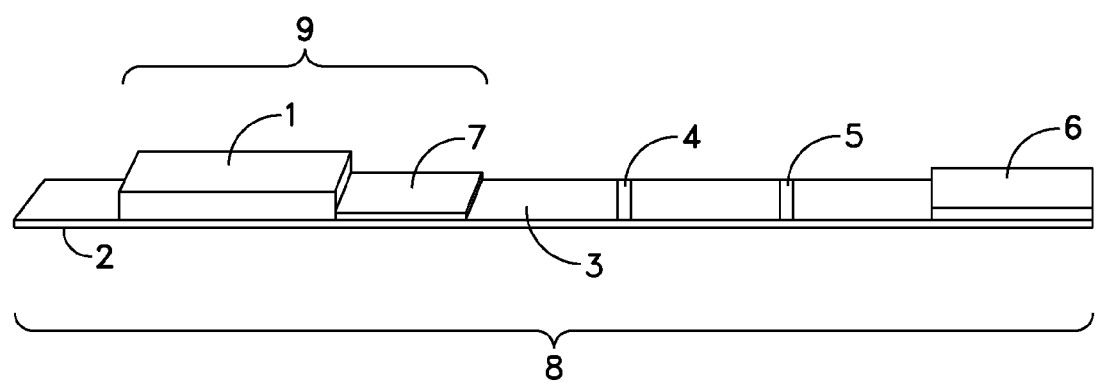
FIG. 1 is a side view of an embodiment having a test zone and a control zone.

We describe herein a method, test strip and method of manufacturing a test strip for detecting one or more analytes in a test sample, such as a milk sample. The method, test strip and method of manufacturing includes combining the sample with both a labeled specific binder and a labeled multianalyte binder to form an admixture. The labeled specific binder can have affinity to fewer than all the analytes to which the multianalyte binder has affinity and the multianalyte binder can have affinity for at least one analyte to which the specific binder has affinity and at least one analyte to which the specific binder has either less affinity than the multianalyte receptor or to which the specific binder lacks affinity. The test can operate when the admixture is contacted with a test strip, the test strip can be configured to allow lateral flow of the admixture from a first end to a second end. The test strip can have a test zone that includes at least two test zone capture agents. A first test zone capture agent can have affinity for the labeled specific binder when the labeled specific binder is unbound by an analyte from the sample and a second test zone capture agent can have affinity for the labeled multianalyte binder when the labeled multianalyte binder is unbound by an analyte from the sample. The admixture can be allowed to flow from the first end to the second end to contact the at least two test zone capture agents. When the admixture contacts the test zone either or both of the labeled binders can be captured at the test zone, when that occurs a detectable signal is emitted from the test zone. The strength of the detectable signal is typically relative to the combined amount of labeled multianalyte binder and labeled specific binder captured in the test zone. In some embodiments the combined amount of the labeled binder captured in the test zone is inversely related to the amount of analyte in the sample. The presence on the test strip, of both the labeled specific binder and the first test zone capture agent, can reduce the test sensitivity to the analyte to which the multianalyte binder has affinity and to which the specific binder does not have affinity. In some aspects the presence on the test strip of both the labeled binders does not decrease test sensitivity to the analyte to which the specific binder has affinity and in some embodiments can increase test sensitivity to such analyte.

In some aspects the specific binder has no functional affinity to the analyte for which the multianalyte binder has affinity and for which the specific binder has less affinity.

Some aspects include a control line. The control line capture agent can have affinity for both the labeled specific binder and the labeled multianalyte binder and be able to bind both said binders whether or not said binders are bound by analyte from the sample. Aspects also include static control lines that provide a standard signal unrelated to the amount of analyte in the sample.

A variety of analytes can be detected using various embodiments including antibiotics such as one or more: beta-lactam antibiotics, tetracycline antibiotics, sulfonamide antibiotics, macrolide antibiotics and aminoglycoside antibiotics.

Specific binders can include various antibodies such as polyclonal and monoclonal antibodies. Multianalyte binders can include various polyclonal antibodies, monoclonal and bacterial receptors.

The multianalyte binder can have affinity to a family of antibiotics and the specific analyte binder can have affinity to a single antibiotic within the same family.

The second test zone capture agent can have affinity for both the specific binder and the multianalyte binder when either binder is unbound from an analyte from the sample. Alternatively, the second test zone capture agent can have affinity for the specific binder and not have affinity for the multianalyte binder.

DESCRIPTION

In an embodiment a test strip includes two different labeled binders, a multianalyte binder and a specific binder. A specific binder can be an antibody or other binding protein or receptor which has affinity to fewer than all analytes to which the multianalyte binder has affinity. A multianalyte binder can be an antibody or other binding protein or receptor with affinity to multiple analytes including the one or more analytes to which the specific binder has affinity and at least one additional analyte to which the specific binder does not have affinity. For example, the specific binder, such as a monoclonal or polyclonal antibody, can have affinity to a particular analyte. The multianalyte binder can have affinity to the analyte to which the specific analyte has affinity and also have affinity for one or more additional analytes. As those skilled in the art will appreciate, the specificity of the specific binder may not be perfect. That is, there may be some cross-reactivity with other analytes. When we describe herein a lack of affinity, we mean lack of affinity to the degree required to be useful in an antibody-antigen binding assay. That may be zero and may be more than zero. That is, the specific binder can have affinity to a single analyte to which the multianalyte binder has similar affinity and have no, or almost no, affinity to other analytes to which the multianalyte binder has affinity. Throughout the specification, when a specific binder is described as not having affinity to an analyte, it is meant the specific binder has relatively less affinity as compared to the multianalyte binder. Typically the affinity will be weak enough as to not be useful in detection of an analyte on an antibody-antigen based lateral flow test strip.

The labeled multianalyte binder and labeled specific binder can be applied to a test strip prior to the sample application. In such embodiments, the sample will combine with the binders on the test strip to form a mobile phase. The labeled binders can also be mixed with the sample and together with the sample added to the test strip in a sample application area. In either case, the combined labeled binders and sample can be referred to as the mobile phase.

A test zone can be composed of two or more different capture agents. Such test zone capture agents can be configured to capture the labeled binder from the mobile phase when unbound by analyte from the sample. One of the capture agents can have affinity to both the multianalyte binder and specific binder and one can have affinity to only the specific binder. Alternatively, each of the capture agents can be specific to a particular binder and not cross-react. For example, one capture agent can be specific to the specific binder and one can be specific to the multianalyte binder.

An optional control line can be configured to include a capture agent that binds both binders with similar affinity, whether or not bound by analyte from the sample. An example of a control line capture agents is an antispecies antibody. A single antispecies antibody is useful when both binders are from the same species. If both binders are not from the same species then more than one control line capture agent may be necessary. Alternatively a "static" control line can be used. Such static control line will bind the labeled binders through a separate binding reaction. In any event, the control line capture agent(s) can have affinity to the binders (or the label or other component associated with the binder) whether or not the binders are bound by analyte.

The methods and devices described herein are particularly useful when a multianalyte binder is overly affinitive, relative to desired detection levels, to one or more analytes. By adding a specific binder that has less affinity or lacks affinity to the analyte to which the multianalyte binder has excess affinity, test sensitivity can be decreased for those analytes to which the specific binder does not have affinity and for which the multianalyte receptor has excessive affinity. At the same time, test sensitivity can be maintained or increased to the analyte for which both the multianalyte binder and specific binder have affinity.

When the specific binder is not bound by analyte from the sample it is available to be captured at the test zone. Capture at the test zone increases the signal intensity at the test zone. The signal in the test zone is inversely related to the quantity of analyte in the sample. When a control line is employed, a comparison is made with the test zone. When the control line intensity is greater than the test zone the test result is positive. That is, one or more analytes is present above a particular level.

The specific binder decreases the sensitivity of the test to the analytes that might bind the multianalyte binder, other than the analyte to which the specific binder has affinity. In some embodiments the multianalyte binder has affinity for the analyte to which the specific binder also has affinity. Test sensitivity will be decreased relative to the analytes for which the multianalyte binder has affinity and to which the specific binder has relatively less, or no, affinity. In that way, test sensitivity can either be maintained or increased relative to the analytes to which the multianalyte binder is not overly affinitive. The decrease in test sensitivity occurs due to the additional background intensity, at the test zone, provided by the specific binder. As a result, it will take relatively more analyte, other than analyte for which the specific binder has affinity, to create a positive result.

In an embodiment a test strip is designed to include a solid support, such as nitrocellulose, and a region for applying a fluid sample ("application area"). Binders and capture agents can be any of a variety of biomolecules e.g., a receptor, enzyme, protein, hormone, or antibody that binds with appropriate affinity and specificity. The binders and the sample, combined often referred to as the mobile phase, can migrate up the test strip, for example, by the forces of lateral capillary flow. During this process the binders bind to any analyte that may be present in the sample to which the binder has affinity. Further upstream the mobile phase contacts the test zone and, if present, the control line. The test zone capture agents can be analyte or analyte analogs adhered to the test strip. A labeled binder that is bound by analyte from the sample tends to bypass the test zone. When a control line is present upstream from the test zone, the binders are then captured at the control line. The control line can include a reagent, adhered to the test strip, which captures both bound and unbound labeled binders.

In an embodiment, the labeled multianalyte binder and labeled specific binder are combined in a solution and applied, for example, by spraying, within or proximate to a pretreated POREX (Porex is a registered trademark of Porex Technologies Corp., Fairburn, Ga.) sample pad. When exposed to a sample, for example of fluid milk, the labeled binders bind to the related sample analyte to form specific binder-analyte complex and multianalyte binder-analyte complex. Lateral capillary flow occurs carrying the analyte complexes, and any unbound binder complex, along a membrane, such as nitrocellulose, to the test zone positioned on the membrane.

The test zone capture agents on the membrane can contain representative analyte, or analyte analog, conjugated to a carrier protein, such as bovine serum albumin (the representative analytes conjugated to bovine serum albumin are the test zone reagents) adhered to the membrane. Such test zone capture agent can include both capture agent for the specific binder and capture agent for the multianalyte binder. Multianalyte binder capture agent can also be capable of capturing the specific binder. Multianalyte bonder can also be specific to multianalyte binder and not be capable of capturing the specific binder. Binders unbound by analyte from the sample bind to the related capture agent on the test zone. Binders bound by analyte from the sample, and excess binders, can flow to a control line and bind to the control line capture agent. A signal visible to the eye or readable with an instrument is generated by the capture at the various lines/zones. In a negative sample the control line will have less binder binding than the test zone. In a positive sample the control line will have more binder binding than the test zone.

Various suitable labels include chromogens, catalysts, fluorescent compounds, chemiluminescent compounds, radioactive labels, magnetic beads or magnetic particles, enzymes or substrates, vesicles containing signal producing substances, colorimetric labels, direct visual labels including colloidal metallic and metallic and non-metallic colored particles, dye particles, or organic polymer latex colored particles.

To detect the presence or absence of an analyte test strips can be designed to provide a signal that can be observed visually, such as color changes or color differences on the test strip. The signal can also be observed, measured and/or interpreted visually or with a reader. A variety of readers are appropriate including spectrophotometers, LCD cameras, reflectance readers, luminometers, fluorometers, scintillation counter, magnetic detectors and other instruments capable of reading, measuring and/or interpreting changes on a lateral flow test strip. One such instrument is described in U.S. Pat. No. 6,124,585, issued Sep. 26, 2000, hereby incorporated by reference. Another such instrument is a ROSA Reader (ROSA is a registered trademark of Charm Sciences, Inc., Lawrence, Mass.).

A variety of materials can be used in various portions of the strip including natural or synthetic materials including cellulosic materials such as paper, cellulose and cellulose derivatives such as cellulose acetate and nitrocellulose; fiberglass; glass fiber filter, for example WHATMAN Fusion 5 membrane (Whatman is a registered trademark of Whatman paper Limited, Kent, England); cloth, both naturally occurring and synthetic; porous gels such as silica gel, agarose, dextran and gelatin; porous fibrous matrices; starch based materials, such as cross-linked dextran chains; ceramic materials; films of polyvinyl chloride and combinations of polyvinyl chloride-silica; POREX and the like. Generally, the material used in the flow stream should allow liquid to flow on or through the strip. If a variety of materials are used they can be in fluid flow communication/contact or capable of being brought into fluid flow communication/contact. The strip should have sufficient inherent strength or additional strength can be provided by a supplemental support such as a plastic backing upon which porous or bibulous strip components are attached.

In an embodiment an application pad is used. The application pad is in fluid flow communication/contact with a first end of a test strip. Contact can be either through direct contact or through an intermediate material allowing flow between the application pad, or application area, and other portions of the test strip. The fluid flow communication/contact is such that the test sample can migrate from the application pad to the other portions of the test strip. In addition to receiving the sample, the application pad can also be used to drive fluid flow along the strip. Particles that are above a certain size may clog the strip pores or may interfere with flow due to affinity to strip components thereby causing invalid or incorrect test results or otherwise reduce test function. The application pad, and other strip components, can also serve as a filter to remove, from the sample, such particles.

In another embodiment, rather than pipette a pre-measured volume onto the strip, the test strip is arranged to be dipped into a sample to absorb a selected amount of the sample.

With a combination of labeled multianalyte binder and labeled specific binder, with test zone capture agents relatively directed to each, test sensitivity can be either maintained or increased for the one or more analytes to which the specific binder has affinity. At the same time, sensitivity of the multianalyte binder to analytes to which it has affinity, and the specific binder does not have affinity, can be reduced.

Typically, a positive result does not inform the user whether the positive result is due to the analyte for which specific binder has affinity or an analyte for which the multianalyte binder has affinity or a combination thereof.

DESCRIPTION OF FIGURES

FIG. 1 shows the test strip apparatus 8, comprised of nitrocellulose membrane 3 and POREX 7 attached to solid support 2. Sample is contacted to sample pad 1. Sample flows from sample pad 1 to POREX 7 containing labeled binders. Binders will bind analyte from the sample and flow along the nitrocellulose membrane 3 to test zone 4. A portion of labeled binders unbound by sample analyte will bind to the related capture agent on the test zone. Remaining unbound labeled binders and labeled binder bound to analyte will flow to control line 5 and be captured. A stronger signal in the control line as compared to the test zone is a positive result. A weaker signal in the control line as compared to the test zone is a negative result.

Figure 2:
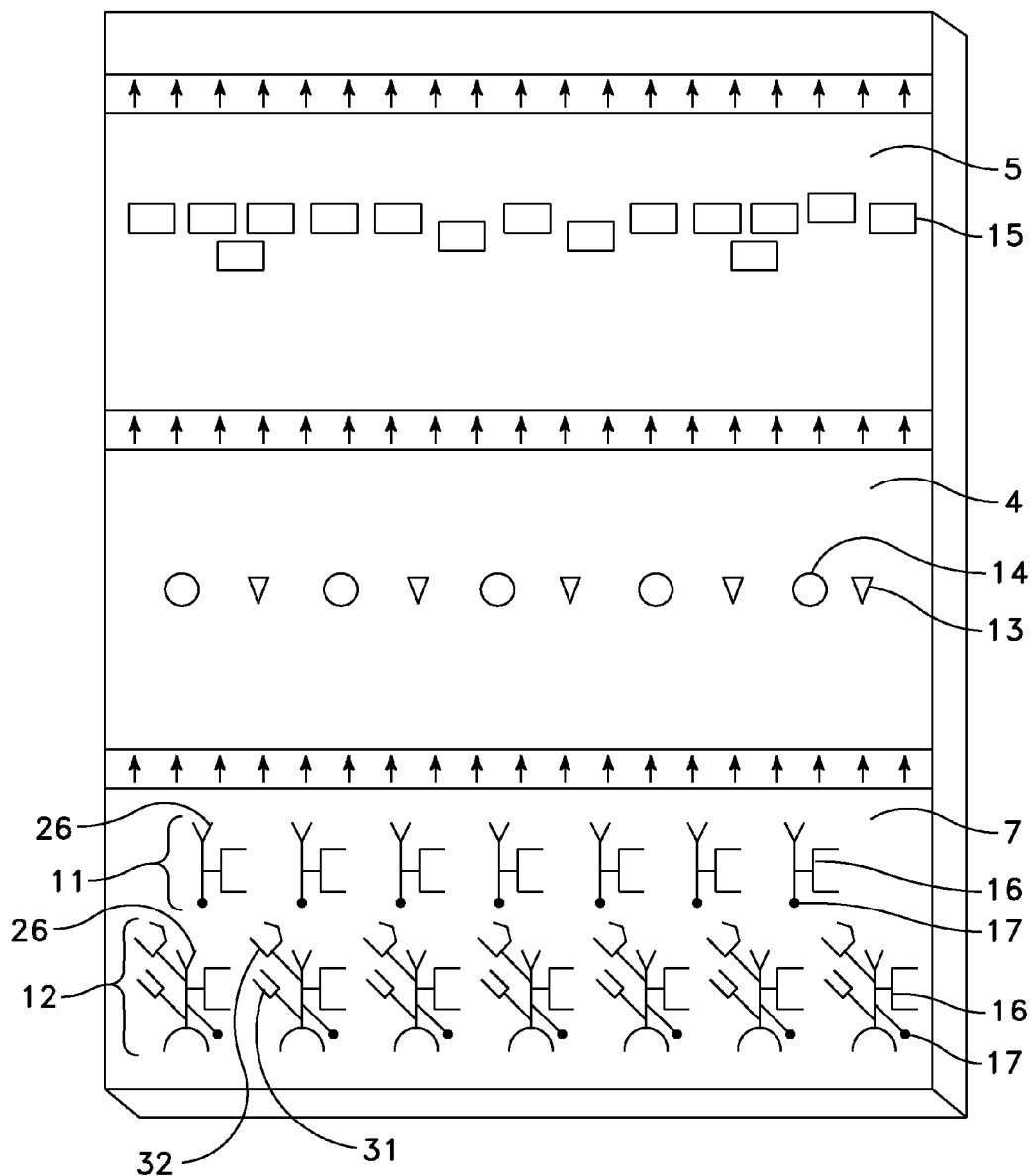
FIG. 2 is a schematic view of the arrangement of test components on the test strip prior to application of sample.

FIG. 2 shows the test strip with the specific binder 11 and multianalyte binder 12 in sample application area 7. Test zone specific binder capture agent 13 and multianalyte binder capture agent 14 are in test zone 4. Control line capture agent 15 is in control line 5 prior to use. Control line capture agent 15 can be an anti-species antibody able to bind either specific binder 11 or multianalyte binder 12 at the species recognition site 16. Also shown is label 17. The binding site 26 for 13 appears in both 11 and 12 in contrast to FIG. 6 in which the binding site 26 for 13 only appears in 11. Additional binding sites 31/32 for additional analytes are also shown relative to the multianalyte binder 12, although the figures do not show analyte binding to those sites. Also not shown is that in some embodiments when analyte binds at either or both sites 31 and 32 of multianalyte receptor, binding to the test zone capture agent can be inhibited although from the figures it appears that such binding at 31 and 32 would not prevent binding of the multianalyte binder at the test zone. For example, it appears in the figures that the binding sites of the multianalyte binder are entirely independent. Some multianalyte binders, for example some polyclonal antibodies may not have entirely separate binding sites. As a result, there can be affinity to multiple analytes although binding to one analyte can inhibit binding to another analyte.

Figure 3:
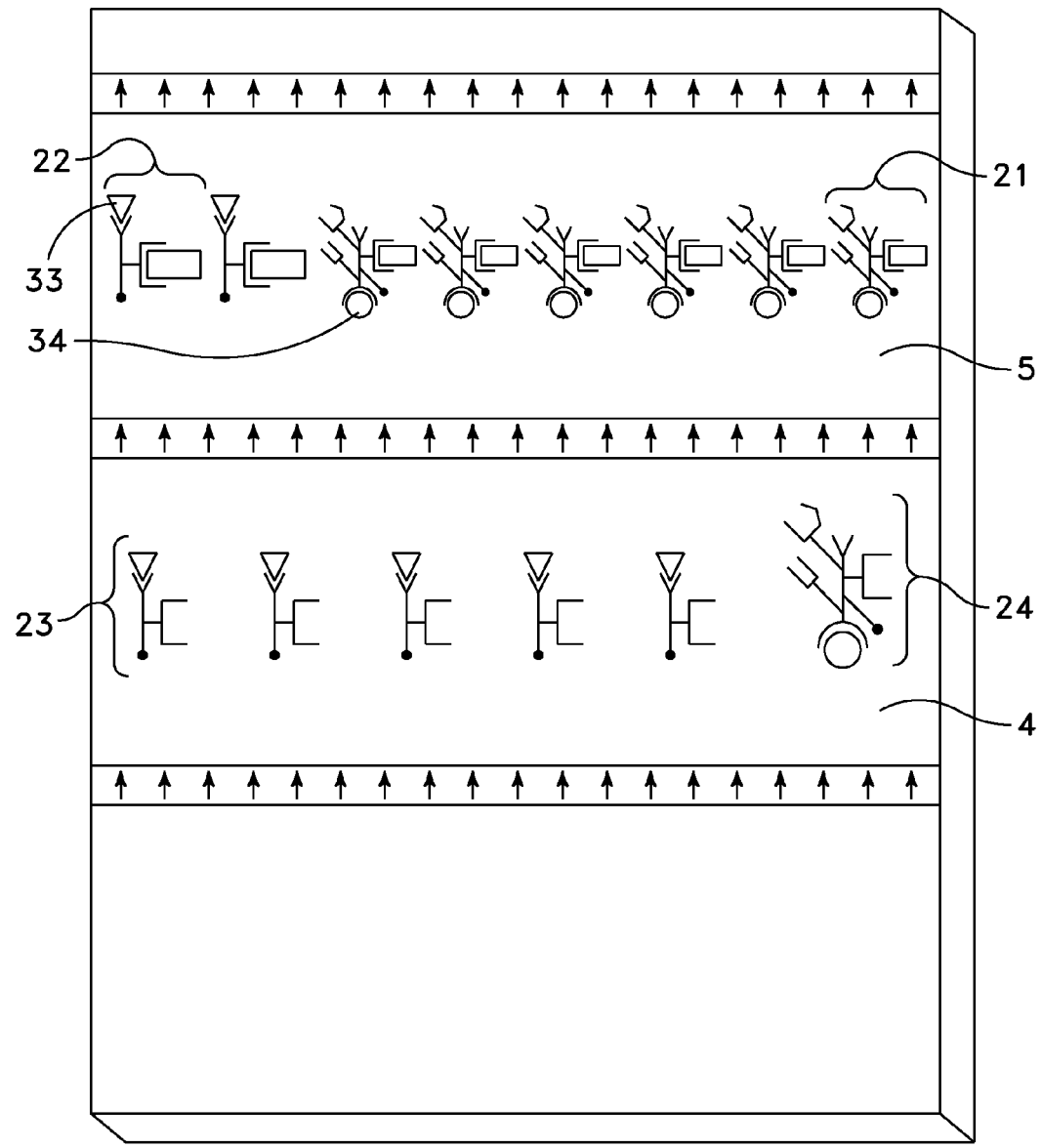
FIG. 3 is a schematic view of test components after application of sample. The movement of test sample fluid and formation of complexes is shown in an example of a test that is positive.

FIG. 3 shows the used test strip with a positive result. Multianalyte binder bound by anti-species binder 21 and specific binder bound by anti-species binder 22 have been captured at the control line and outnumber specific binder and multianalyte binder captured 23/24 at the test line 4. Multianalyte binder is shown as analyte-bound 34 and specific binder is shown in as analytye-bound 33. Such binding by analyte prevents capture at the test zone. Not shown is that the test can be configured so that some amount of labeled multianalyte and specific binder will flow to the control line even in a sample with no amount of analyte. What is shown is that all binders captured at the control line have been bound by analyte from the sample thereby inhibiting binding at the test zone.

Figure 4:
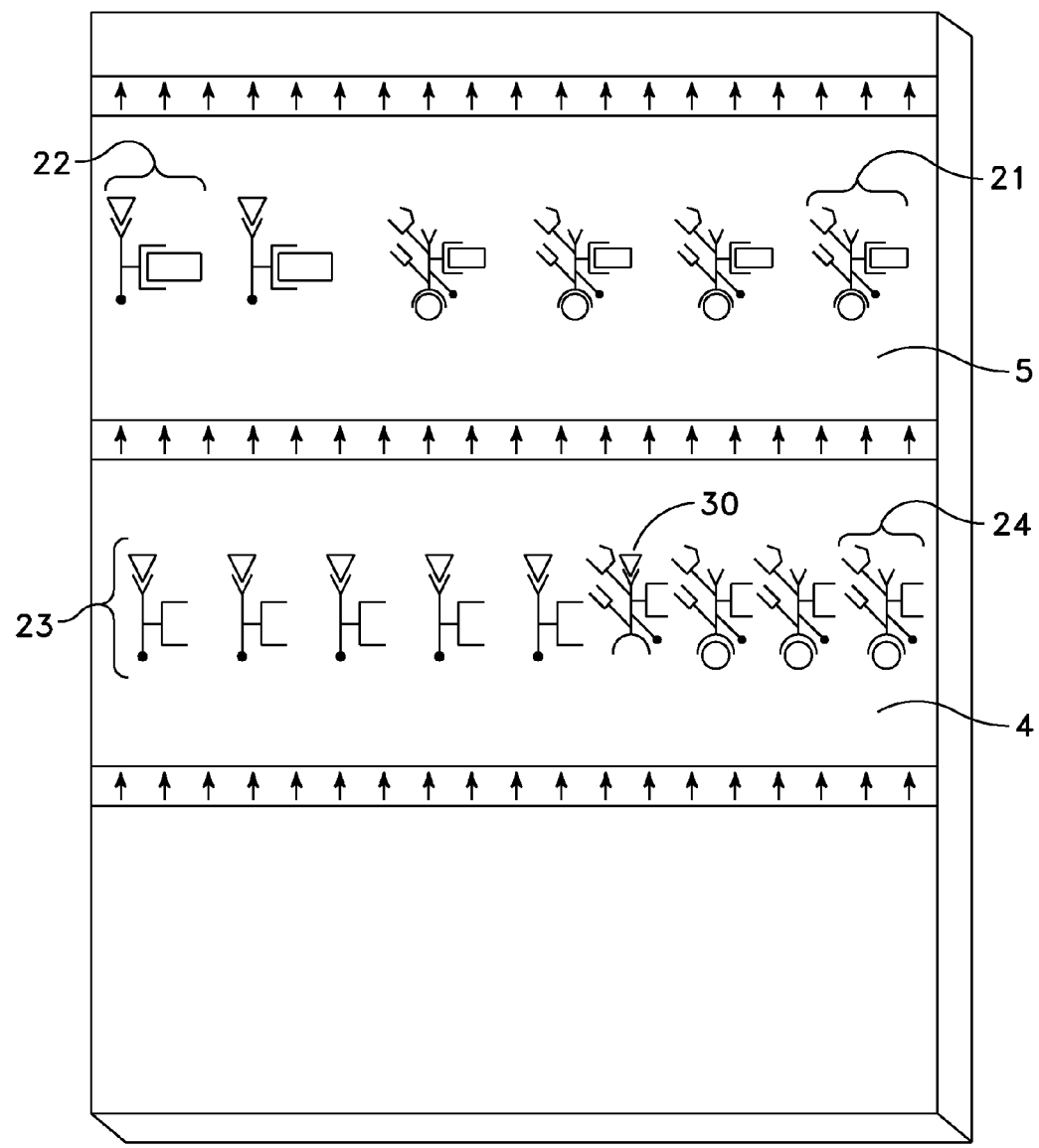
FIG. 4 is a schematic view of test components after application of sample. Movement of fluid and formation of complexes is shown in an example of a test that is negative.

FIG. 4 shows the used test strip with a negative result; some analyte is present although not enough to produce a positive result. More labeled binder is captured 23/24 at the test line 4 compared to those captured 21/22 at the control line 5. As in FIG. 3, not shown is that the test can be configured so that some amount of unbound, labeled multianalyte and specific binder can flow to control line 5 even in a sample with no amount of analyte. What is shown is that all binders captured at the control line have been bound by analyte from the sample thereby inhibiting binding at the test zone. Also shown is multianalyte binder 24 being captured at test zone by specific binder test zone capture agent 30. That is possible when multianalyte binder has affinity to the same test zone capture agent as specific binder, which is not the case in FIG. 6.

Figure 5:
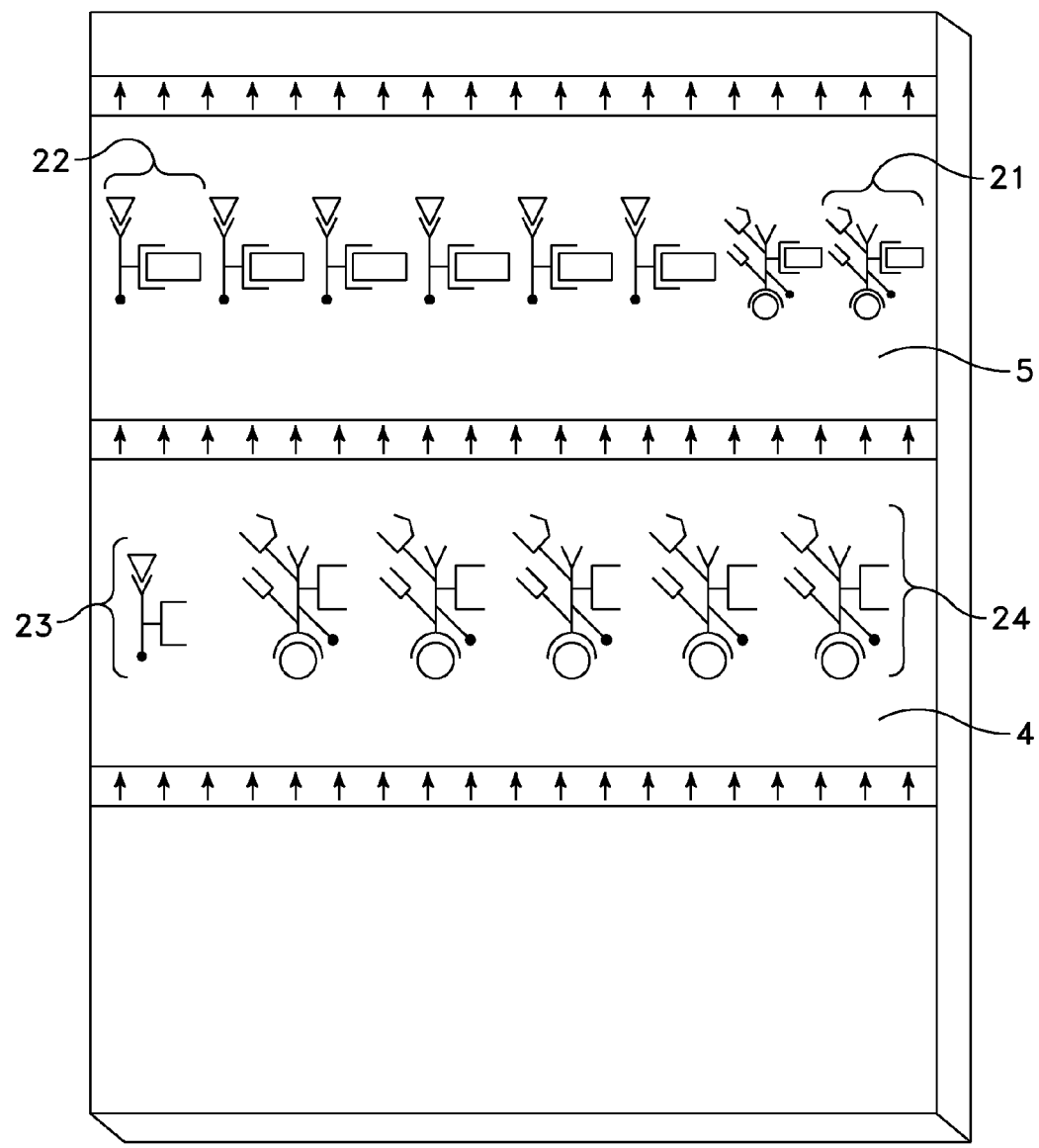
FIG. 5 is a schematic view of test components after application of sample. Movement of fluid and formation of complexes is shown in an example of a test that is positive.

FIG. 5 shows the used test strip with a positive result. Multianalyte binder bound by anti-species binder 21 and specific binder bound by anti-species binder 22 have been captured at the control line and outnumber specific binder and multianalyte binder captured 23/24 at the test line 4.

Figure 6:
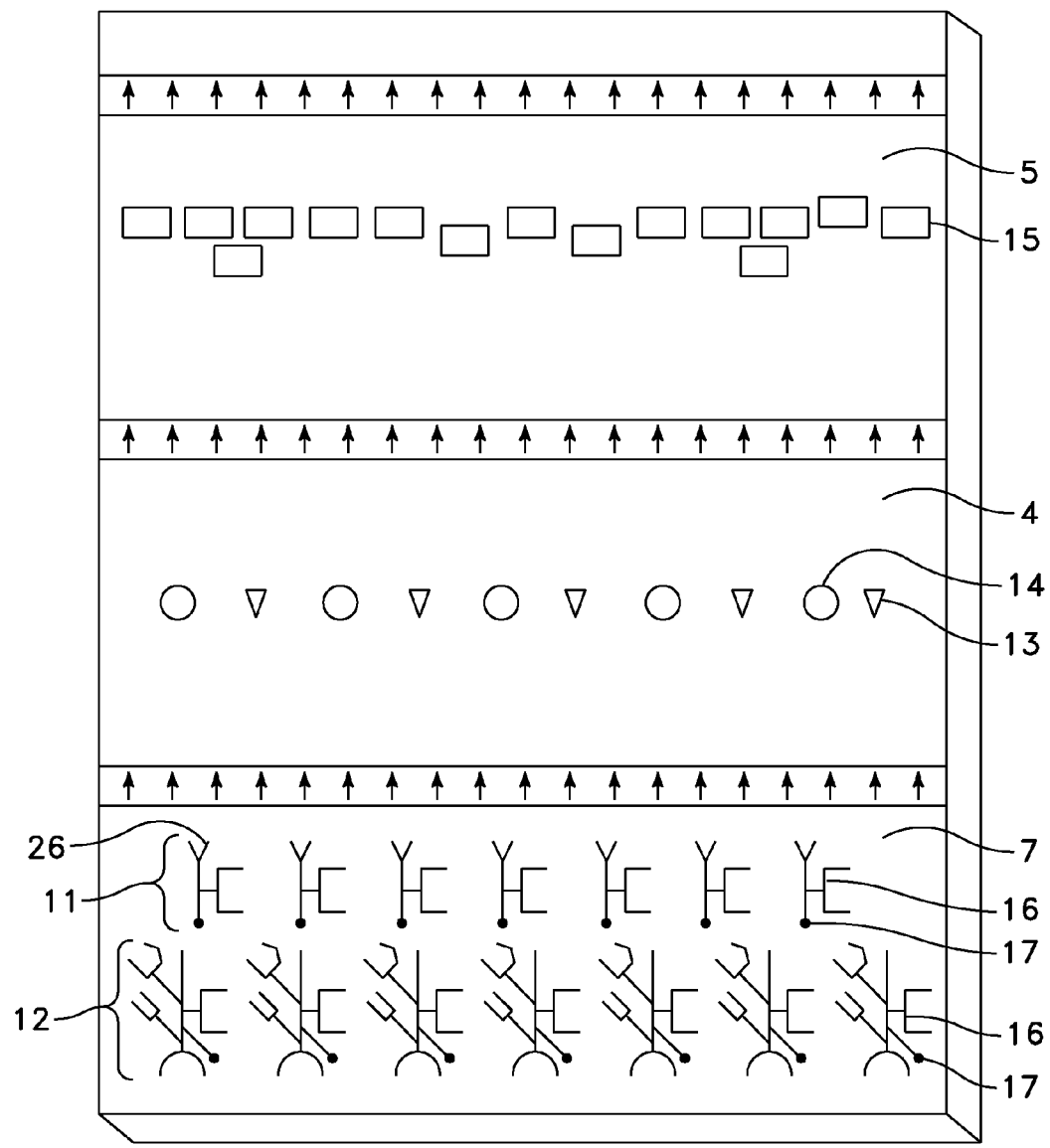
FIG. 6 is a schematic view of test components before application of sample. In contrast to FIG. 2, multianalyte binder does not have affinity to both test zone capture agents.

FIG. 6 shows an alternative embodiment of the test strip with the specific binder 11 and multianalyte binder 12, test zone capture agent for specific binder 13 and multianalyte binder 14 and control line capture agent 15, prior to use. Control line capture agent 15 can be an anti-species antibody able to bind either specific binder 11 or multianalyte binder 12 at the species recognition site 16. The binding site 26 for 13 appears only in 11 in contrast to FIG. 2 in which the binding site for 13 appears in both 11 and 12.

The invention claimed is:

1. A method for detecting at least two analytes, when present, in a test sample, said method comprising:
    a) combining the sample with both a labeled specific binder and a labeled multianalyte binder to form an admixture, the specific binder having affinity to at least a first analyte but fewer than all the analytes to which the multianalyte binder has affinity and the multianalyte binder having affinity for (i) the at least one first analyte to which the specific binder has affinity and (ii) at least one second analyte to which the specific binder has less affinity than does the multianalyte binder;
    b) contacting the admixture with a test strip, the test strip configured to allow lateral flow of the admixture from a first end of the test strip to a second end of the test strip, the test strip having a test zone capable of capturing both the specific binder and the multianalyte binder, the test zone comprising at least two test zone capture agents, a first test zone capture agent having affinity for the specific binder when the specific binder is unbound by an analyte from the sample and a second test zone capture agent having affinity for the multianalyte binder when the multianalyte binder is unbound by an analyte from the sample;
    c) allowing the admixture to flow from the first end to the second end to contact the at least two test zone capture agents, wherein when any of the binders are captured at the test zone a detectable signal occurs in the test zone, the strength of which signal is relative to the combined amount of multianalyte binder and specific binder captured in the test zone, and
    wherein the combined amount of the multianalyte and specific binders captured in the test zone is inversely related to the total amount of analyte in the sample and wherein the presence on the test strip of both the specific binder and the first test zone capture agent (i) reduces the test sensitivity to the second analyte to which the multianalyte binder has affinity and to which the specific binder does not have affinity (ii) and increases test sensitivity to the first analyte to which the specific binder has affinity.

2. The method of claim 1 wherein the presence of both the specific binder and the first test zone capture agent increases the sensitivity of the test to the analyte for which both the specific binder and the multianalyte binder have affinity.

3. The method of claim 1 wherein the specific binder has no affinity to the analyte for which the multianalyte binder has affinity and for which the specific binder has less affinity.

4. The method of claim 1 further comprising allowing the admixture to contact a control line on the test strip, the control line comprising a control line capture agent, the control line capture agent having affinity for both the specific binder and the multianalyte binder and able to bind both said binders whether or not said binders are bound by analyte from the sample, wherein the amount of binder captured at the control line can be compared to the amount of binder captured at the test line and wherein when positive result occurs when more binder is captured at the control line than the test line.

5. The method of claim 1 wherein the one or more analytes are selected from the group consisting of a beta-lactam antibiotic, a tetracycline antibiotic, a sulfonamide antibiotic, a macrolide antibiotic and an aminoglycoside antibiotic.

6. The method of claim 1 wherein both the specific binder and the multianalyte binder are polyclonal antibodies.

7. The method of claim 1 wherein the specific binder comprises a monoclonal antibody and wherein the multianalyte binder comprises a polyclonal antibody.

8. The method of claim 1 wherein the specific binder comprises an antibody and wherein the multianalyte binder comprises a bacterial receptor.

9. The method of claim 1 wherein the multianalyte binder has affinity to a family of antibiotics and the specific binder has affinity to a single antibiotic within the same family.

10. The method of claim 1 wherein the second test zone capture agent has affinity for both the specific binder and the multianalyte binder when either binder is unbound from an analyte from the sample.

11. The method of claim 1 wherein the second test zone capture agent has affinity for the specific binder and does not have affinity for the multianalyte binder.

12. A lateral flow test strip to detect at least two analytes, when present, in a test sample, the test strip configured to allow a test solution to flow from a first end of the test strip to a second end of the test strip, and comprising:
    a) a sample application area at the first end, the sample application area comprising at least two labeled binders configured to flow on the test strip when contacted with the sample, a first labeled binder being a specific binder, the specific binder having affinity to at least a first analyte but fewer than all the analytes to which a labeled multianalyte binder has affinity and a second labeled binder being the labeled multianalyte binder, the multianalyte binder having affinity for the at least one first analyte to which the specific binder has affinity and at least one second analyte to which the specific binder has less affinity than does the multianalyte binder; and b) a test zone capable of capturing both the specific binder and the multianalyte binder, the test zone comprising at least two test zone capture agents, a first test zone capture agent having affinity for the specific binder when unbound by analyte from the sample and a second test zone capture agent having affinity for the multianalyte binder when unbound by analyte from the sample, wherein the test solution and both the labeled binders flow from the sample application area to the test zone and wherein the amount of the multianalyte and specific binders captured in the test zone is inversely related to the amount of analyte in the sample and wherein the presence of the specific binder and the first test zone capture agent reduces the sensitivity of the test for the second analyte to which the specific binder has less affinity than does the multianalyte binder and increases test sensitivity to the first analyte for which the specific binder has affinity.

13. The test strip of claim 12 wherein the presence of both the specific binder and the first test zone capture agent increases the sensitivity of the test to the analyte for which both the specific binder and the multianalyte binder have affinity.

14. The test strip of claim 12 wherein the specific binder has no affinity to the analyte for which the multianalyte binder has affinity and for which the specific binder has less affinity.

15. The test strip of claim 12 further comprising a control line, the control line comprising a control line capture agent, the control line capture agent having affinity for both the specific binder and the multianalyte binder and able to bind both said binders whether or not said binders are bound by analyte from the sample.

16. The test strip of claim 12 wherein the multianalyte binder has affinity to a family of antibiotics and the specific binder has affinity to a single antibiotic within the same family.

17. The test strip of claim 12 wherein the presence together on the test strip of the specific binder and the first capture agent reduces the test sensitivity to any of the analytes to which the multianalyte binder has affinity and to which the specific binder has less affinity or no affinity.

18. The test strip of claim 12 wherein both the specific binder and the multianalyte binder are polyclonal antibodies.

19. The test strip of claim 12 wherein the specific binder comprises a monoclonal antibody and wherein the multianalyte binder comprises a polyclonal antibody.

20. The test strip of claim 12 wherein the specific binder comprises an antibody and wherein the multianalyte binder comprises a bacterial receptor.

21. The method of claim 12 wherein the one or multiple analytes are selected from the group consisting of a beta-lactam antibiotic, a tetracycline antibiotic, a sulfonamide antibiotic, a macrolide antibiotic and an aminoglycoside antibiotic.

22. A method for manufacturing a test strip with sensitivity to at least two analytes, when present, in a fluid sample, said method comprising:

a) combining a labeled multianalyte binder and a labeled specific binder to form a binder admixture, the multianalyte binder characterized by (i) an affinity to at least one first analyte to which the specific binder has affinity and (ii) at least one second analyte to which the specific binder has less affinity than does the multianalyte binder;

b) applying, to a sample application area of a test strip, the binder admixture, the binder admixture configured to flow on the test strip, when combined with the sample, from the application area to a test zone on the strip;

c) attaching at least two capture agents to the test zone, the first test zone capture agent having affinity for the specific binder when unbound by analyte from the sample and a second test zone capture agent having affinity for the multianalyte binder when the multianalyte binder is unbound by analyte from the sample, and wherein when a test sample is added to the sample application area the binder admixture flows, with the test solution, from the sample application area to the test zone and wherein the combined amount of the multianalyte and specific binders bound to the test zone is inversely related to the total amount of analyte in the sample and wherein the test sensitivity is reduced to an analyte, other than the analyte to which the specific binder has affinity, and the test sensitivity is not reduced to the analyte for which the specific binder has affinity.

23. The method of claim 22 wherein the first test zone capture agent has affinity for both the specific binder and the multianalyte binder when either binder is unbound by analyte from the sample.

24. The method of claim 22 wherein the second test zone capture agent has affinity for the unbound specific binder and does not have affinity for the unbound multianalyte binder.

25. The method of claim 22 wherein the presence of both the specific binder and the first test zone capture agent increases the sensitivity of the test to the analyte for which both the specific binder and the multianalyte binder have affinity.

26. The method of claim 22 wherein the specific binder has no affinity to the analyte for which the multianalyte binder has affinity and the specific binder has less affinity.

27. The method of claim 22 further comprising attaching a control line capture agent to a control line on the test strip, the control line capture agent having affinity for both the specific binder and the multianalyte binder and able to bind both said binders whether or not said binders are bound by analyte from the sample.

28. The method of claim 22 wherein both the specific binder and the multianalyte binder are polyclonal antibodies.

29. The method of claim 22 wherein the specific binder comprises a monoclonal antibody and wherein the multianalyte binder comprises a polyclonal antibody.

30. The method of claim 22 wherein the specific binder comprises an antibody and wherein the multianalyte binder comprises a bacterial receptor.

31. The method of claim 22 wherein the labeled multianalyte binder has affinity to a family of antibiotics and the specific analyte binder has affinity to a single antibiotic within the same family.

32. The method of claim 22 wherein the one or more analytes are selected from the group consisting of a beta-lactam antibiotic, a tetracycline antibiotic, a sulfonamide antibiotic, a macrolide antibiotic and an aminoglycoside antibiotic.

* * * * *